United States Patent [19]

Aster et al.

[11] Patent Number: 5,585,243
[45] Date of Patent: Dec. 17, 1996

[54] METHOD OF DETECTING CYTOPENIA THAT IS MEDIATED BY DRUG-DEPENDENT ANTIBODY BINDING TO BLOOD CELLS

[75] Inventors: Richard H. Aster, Milwaukee; Brian R. Curtis, Port Washington, both of Wis.

[73] Assignee: The Blood Center of Southeastern Wisconsin, Inc., Milwaukee, Wis.

[21] Appl. No.: 120,837

[22] Filed: Sep. 15, 1993

[51] Int. Cl.$^6$ ............................................. G01N 33/567
[52] U.S. Cl. .................. 435/7.21; 435/7.2; 435/7.24; 435/7.25; 435/7.9; 435/7.92; 435/7.95; 436/519; 436/520
[58] Field of Search ................................ 435/7.21, 7.2, 435/7.24, 7.92, 7.95, 7.25, 7.9; 436/519, 520

[56] References Cited

U.S. PATENT DOCUMENTS 4,717,654  1/1988  Savoca et al. ........................... 435/7

FOREIGN PATENT DOCUMENTS 9202823  2/1992  WIPO .

OTHER PUBLICATIONS

Logue et al., New England Journal of Medicine, vol. 283 No. 17, pp. 900–904 (Oct. 22, 1970).
Levitt, Blood, vol. 69 No. 2, pp. 394–400 (Feb. 1987).
A. V. Pisciotta et al, "Cytotoxic Activity In Serum of Patients With Clozapine–Induced Agranulocytosis", *J. Lab. Clin. Med.* 119(3):254–266 (1992).
A. Salama et al, "Immune–mediated Agranulocytosis Related to Drugs and Their Metabolites: Mode of Sensitization and Heterogeneity of Antibodies", *Br. J. of Haematology* 72:127–132 (1989).
H. E. Hamilton et al, "Sulfisoxazole–Induced Thrombocytopenic Purpura", *JAMA* 238(24):2586–2587 (1978).
F. W. A. Verheugt et al, "Autoimmune Granulocytopenia: the Detection of Granulocyte Autoantibodies with the Immunoflourescence Test", *Br. J. of Haematology* 39:339–350 (1978).
G. P. Visentin et al, "Detection of Drug–Dependent, Platelet–Reactive Antibodies by Antigen–Capture ELISA and Flow Cytometry", *Transfusion* 30(8):694–700 (1990).
S. A. Weitzman et al, "Drug–Induced Immunological Neutropenia", *The Lancet* 1068–1071 (May 20, 1978).
C. H. Packman et al, "Drug–Related Immunologic Injury of Erythrocytes", in W. J. Williams et al (eds.) *Hematology* Chapter 69:681–686 (4th edition McGraw Hill 1990).
S. Karpatkin, "Drug–Induced Thrombocytopenia", *The American J. of The Medical Sciences* 262(2):68–78 (1971).
T. Hackett et al, "Drug–Induced Platelet Destruction", *Seminars in Thrombosis and Hemostasis* 8(2): (1982). pp. 116–137.
B. H. Chong, "Drug–Induced Immune Thrombocytopenia", *Platelets*, 2: 173–181 (1991).

C. Mueller–Eckhardt et al, "Drug–Induced Immune Cytopenias: A Unifying Pathogenetic Concept With Special Emphasis on the Role of Drug Metabolites", *Transfusion Medicine Reviews* 4(1):69–77 (1990).
J. N. George, "Drug–Induced Immunologic Thrombocytopenia", in W. J. Williams et al (eds.) *Hematology* Chapter 130:50–64.
V. Kiefel et al, "Metabolite–Specific (IgG) and Drug–Specific Antibodies (IgG, IgM) in Two Cases of Trimethoprim-Sulfamethoxasole–Induced . . . ", *Transfusion* 27(3):262–265 (1987).
M. Karpatkin et al, "The Platelet Factor 3 Immunoinjury technique Re–evaluated . . . ", *J. Lab. Clin. Med.* 80(2):400–408 (1977).
P. L. Cimo et al, "Detection of Drug–Dependent Antibodies by the $^{51}$Cr Platelet Lysis Test", *Amer. J. of Hematology* 2:65–72 (1977).
J. G. Kelton et al, "Drug–Induced Thrombocytopenia is Associated With Increased Binding of IgG to Platelets Both In Vivo and In Vitro", *Blood* 58(3):524–529 (1981).
J. E. Menitove et al, "Cyclic Thrombocytopenia of Apparent Autoimmune Etiology", *Blood* 73(6):1561–1569 (1989).
A. Salama et al, "Immune–Mediated Blood Cell Dyscrasias Related to Drugs", *Seminars in Hematology* 29(1):54–63 (1992).
N. R. Shulman et al, "Platelet Immunology", in R. W. Coleman et al (eds.) *Hemostasis and Thrombosis* (second edition J.B. Lippincott Co.) Chapter 27:452–529 (1987).
"Thrombocytopenia Due to Platelet Destruction and Hypersplenism", in R. Hoffman et al (eds.) *Hematology Basic Principles and Practice* (Churchill Livingstone) Chapter 125: 1505–1507 (1991).
P. Handagama et al, "Thrombocytopenia and Drugs", *Vetern. Clin. of N. Amer.: Small Animal Practice* 18(1) 51–65 (1988).
D. F. Stroncek et al, "Quinine–Dependent Antibodies to Neutrophils React With a 60–Kd Glycoprotein on Which Neutrophil–Specific Antigen NB1 is Located . . . ", *Blood* 81(10): 2758–2766 (1993).
B. C. Gilliland, "Drug–Induced Autoimmune and Hematologic Disorders", *Immunology and Allergy Clinics of North America* 11(3):525–553 (1991).
G. P. Visentin et al, "Characteristics of Quinine– and Quinine–Induced Antibodies Specific For Platelet Glycoproteins IIb and IIIa", *Blood* 77(12):2668–2676 (1991).
P. Finley et al "Flow Cytometry Analysis of Platelet Antibodies" in Journal of Clinical Laboratory Analysis vol. 2 No. 4 (1988) pp. 249–255.
D. Christie et al "Detection of Drug–Dependent Platelet Antibodies Using Immobilized Staphylococcal Protein A", Transfusion v. 28. No. 4 (1988) pp. 322–325.
J. Gottschall et al., "Quinine–Induced . . . Thrombocytopenia . . . " Blood, vol. 77, No. 2 (Jan. 15, 1991): pp. 306–310.
Hackh's Chemical Dictionary (fourth edition 1969); pp. 563–564 "Quinidine" and Quinine.

*Primary Examiner*—Carol A. Spiegel
*Attorney, Agent, or Firm*—Foley & Lardner

[57] ABSTRACT

Drug-dependent antibodies that bind to granulocytes, erythrocytes, platelets or membrane proteins derived from these cells, in the presence of a drug, but not in its absence, can be detected using a sensitive assay. Detection of the drug-dependent antibodies permits diagnosis of cytopenia mediated by the drug.

19 Claims, 5 Drawing Sheets

FIG. 1A  PATIENT SERUM (H.W.) + PHENYTOIN IN BUFFER
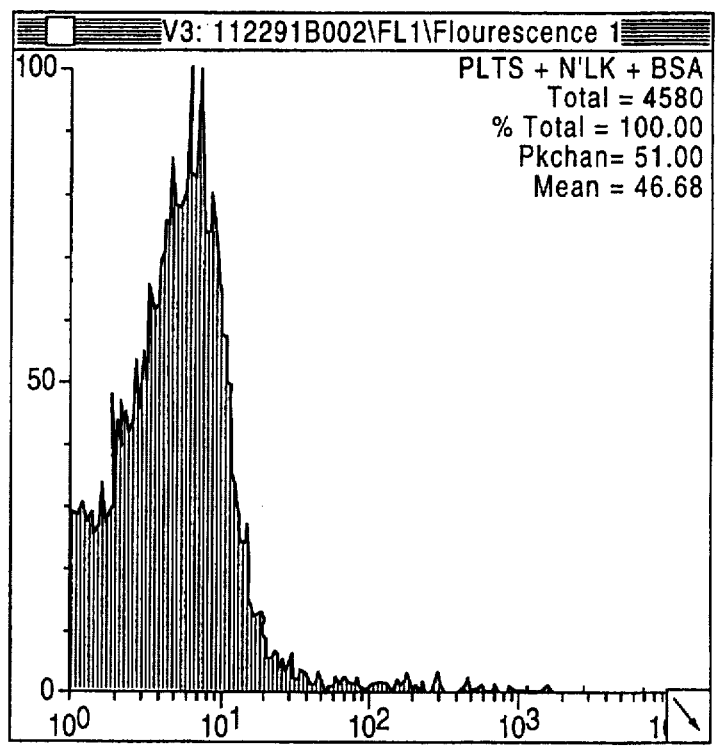
FIG. 1C  PATIENT SERUM (HW) + 5% BSA (NO DRUG PRESENT)
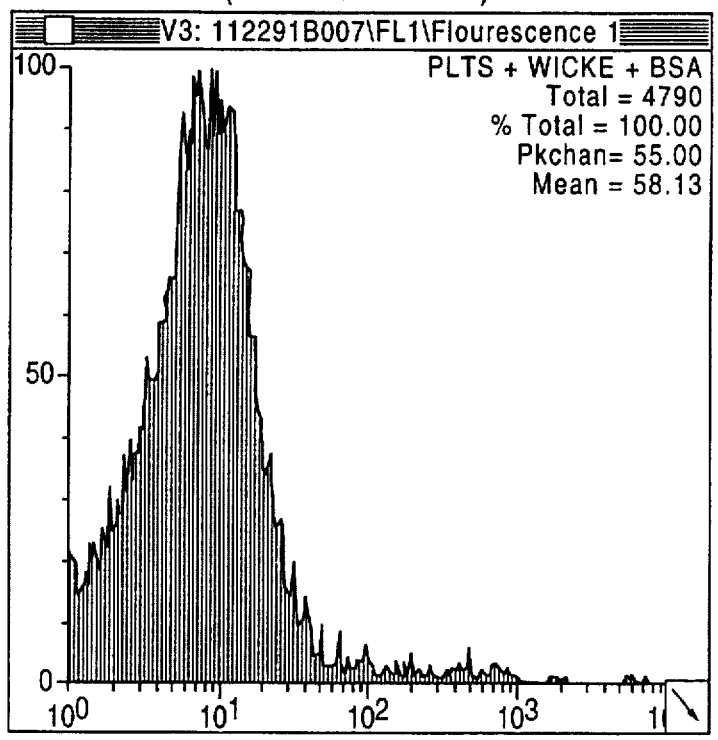

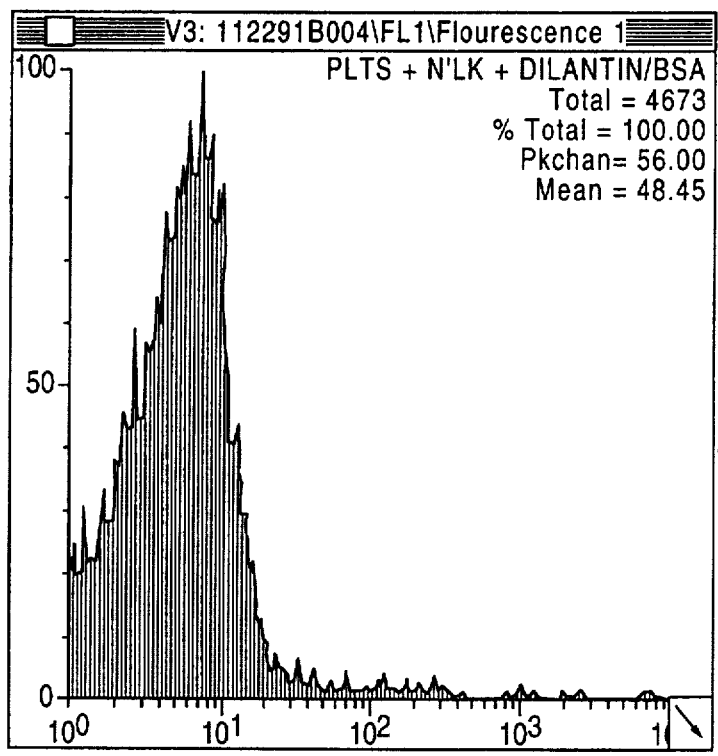
FIG. 1B NORMAL SERUM (L.K.) + PHENYTOIN DISSOLVED IN 5% BSA
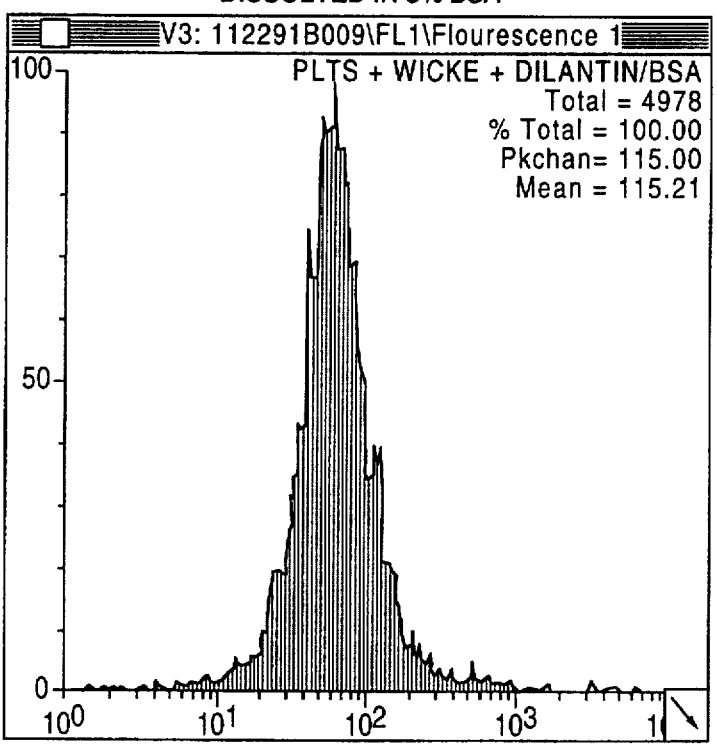
FIG. 1D PATIENT SERUM (HW) + PHENYTOIN DISSOLVED IN 5% BSA

PATIENT SERUM + GRANULOCYTES + BUFFER (NO DRUG PRESENT)

PATIENT SERUM + GRANULOCYTES + 0.2 mM QUININE (DRUG)

METHOD OF DETECTING CYTOPENIA THAT IS MEDIATED BY DRUG-DEPENDENT ANTIBODY BINDING TO BLOOD CELLS

BACKGROUND OF THE INVENTION

The present invention relates to a sensitive method for detecting drug-induced cytopenia mediated by antibodies that bind to blood cells or platelets only in the presence of a drug. Antibodies that react with blood cells or platelets only in the presence of an inciting drug are called "drug-dependent antibodies" (DDAb). This method also identifies the drug that is mediating the cytopenia in a particular patient.

A wide variety of medications have been implicated in the pathogenesis of drug-induced cytopenia (DIC). Cytopenia is a reduction or a lack of granulocytes, erythrocytes or platelets in the circulating blood. The particular cytopenias for which drug-dependent antibody binding can be identified using the method of the present invention include: granulocytopenia, also called agranulocytosis or neutropenia or leukopenia; thrombocytopenia; and hemolytic anemia.

Granulocytopenia is the clinical condition that exists when a patient has less than the normal number of granular leukocytes, usually neutrophils, in the blood. Thrombocytopenia is the clinical condition that exists when a patient has an abnormally small number of platelets in the circulating blood. Hemolytic anemia is a clinical condition in which the number of red blood cells in a patient's peripheral blood are less than normal due to abnormal destruction of erythrocytes in the body.

The main hindrance in diagnosing drug-induced antibody dependent cytopenia resides in the difficulty of objectively identifying the drug that is causing the cytopenia. The most widely used method of diagnosing drug-induced cytopenia is an indirect test that merely removes all medications that the cytopenic patient may be taking. If the patient's cytopenia resolves after drug removal, then the drug is said to be "associated" or "implicated" in causing the cytopenia.

Indirect implication of a drug in the pathogenesis of a patient's cytopenia is particularly problematic when a patient is on a regimen involving multiple medications, any one of which may be essential to treating a serious clinical condition. In vivo rechallenge with the suspected drug usually poses too great a potential risk. A method for identifying the one medication that is causing the cytopenia is needed so that the physician need not terminate administration of a cytopenic patient's needed, non-deleterious medications. Therefore, an in vitro test is needed to demonstrate the presence of an antibody in the patient's serum that binds to normal platelets, granulocytes or erythrocytes only in the presence of the offending drug, but not in the drug's absence.

More than 100 medications have been implicated in the pathogenesis of drug-dependent cytopenias, yet drug-dependent antibody binding has only been shown to be the pathogenetic mechanism underlying cytopenia in a few instances. These few instances include: (1) the detection of antibody binding to platelets which is dependent on the following drugs in the pathogenesis of thrombocytopenia: quinine, quinidine, acetaminophen, acetaminophen metabolites, Cefotetan, diphenylhydantoin, diazepam, novobiocin, penicillin, rifampin, vancomycin, valproic acid, cyanidanol, procainamide, sulfisoxazole, sulfamethoxazole, sulfamethoxazole metabolites, Para-aminosalicylic Acid (PAS), PAS metabolites and stibophen; Kelton et al., *Blood* 58:524 (1981); Cimo, et al., *Am. J. Hematol.* 2: 65 (1977); Hamilton et al., *JAMA* 239: 2586 (1978); Visentin et al., *Transfusion* 30:694 (1990); Kieffel, et al., *Transfusion* 27:262 (1987); and Aster et al., in Williams et al., (eds.) HEMATOLOGY (4th edition, McGraw Hill, 1990); (2) the detection of penicillin, Nafcillin, Oxacillin, propylthiouracil, propyphenazone and amodiaquine-dependent antibody binding to granulocytes in the pathogenesis of granulocytopenia; Salama et al., *Br. J. Haematol.* 72: 127 (1989); (Weitzman et al., *Lancet* 1: 1068 (1978); (Fibbe et al., *Br. J. Haematol.* 64: 363 (1986); (Salama et al., supra); (Rouveix et al., *Br. J. Haematol.* 71: 7 (1989); and (3) the detection of Ceftazidime, Cefotetan and diclofenac-dependent antibody binding to human erythrocytes in the pathogenesis of hemolytic anemia; Chambers et al., *Am. J. Clin. Pathol.* 95: 393 (1991); and Salama et al., *Br. J. Haematol.* 77: 546 (1991).

With the exception of the few instances of drug-dependent antibody binding to granulocytes, erythrocytes or platelets elucidated above, there has not been a reliable objective test for identifying drug-dependent antibody binding to granulocytes (G), erythrocytes (E) or platelets (P) (hereinafter referred to as GEP). The current assay systems have the major problems of resulting in false negative or false positive results. Some studies have reported results that suggest antibodies are not involved in a particular patient's cytopenia or in particular types of cytopenias. For example, no antibody binding could be demonstrated in a granulocytopenic patient who had been taking phenytoin. Sharafuddin et al., *Acta Haematol.* 86: 212 (1991). Also, in patients with clozapine-induced agranulocytosis, no drug-dependent antibody binding to granulocytes could be demonstrated. Pisciota et al., *J. Lab. Clin. Med.* 119: 254 (1992).

Prior art assays for the detection of antibody binding to granulocytes, such as the granulocyte immunofluorescence test (GIFT), are unable to demonstrate drug-dependent antibodies because of: (a) false negative results; (b) false positive results (no drug dependent binding of antibody); and (c) high background fluorescence. With many drugs, false negative results are probably due to the drug being unavailable in the reaction due to its insolubility in the buffer system. False positive results due to the drug alone increasing fluorescence are often the result of the insensitivity of prior art assays which required high concentrations of drug in order to detect drug-dependent antibody binding.

Thus, the diagnosis of drug-dependent antibody-mediated cytopenia has been difficult because there has not been a reliable in vitro method for detecting antibodies that are present in a cytopenic patient's serum and bind to blood cells or platelets only in the presence of a drug. A need exists for a reliable, objective method for detecting drug-dependent antibody binding to GEP in order to identify the particular drug causing a patient's cytopenia.

SUMMARY OF THE INVENTION

The present invention is based upon the discovery of a particular approach for reliably detecting drug-dependent antibody binding to granulocytes, erythrocytes and platelets employing a solubilized drug and a highly sensitive assay system. Further, it has been discovered that, by insuring that the implicated drug is solubilized in the assay system, heretofore undetected drug-dependent antibody binding to human GEP can now be determined.

Thus, the invention relates to a method of detecting drug-dependent antibody binding to human GEP.

It is therefore an object of the present invention to provide a sensitive method for detecting drug-dependent antibody binding to human GEP, especially for drugs previously implicated yet never directly shown to mediate cytopenia using the previously available assay systems.

It is a further object of the present invention to identify drug-dependent antibodies that only react with granulocytes, erythrocytes or platelets in the presence of a sparingly water soluble drug.

It is also an object of the present invention to identify the specific drug responsible for a patient's suspected drug-induced cytopenia, to avoid unnecessary withdrawal of other needed drugs.

It is a further object of the present invention to provide an extremely sensitive method for detecting even low titers of drug-dependent antibodies that bind to GEP.

In accomplishing these and other objects, there has been provided, in accordance with one aspect of the present invention, a method of detecting drug-dependent antibody binding to human granulocytes, erythrocytes or platelets, comprising the steps of: (a) incubating human granulocytes, erythrocytes or platelets with a patient serum or plasma sample, both in the presence and in the absence of a drug suspected of inducing cytopenia; and (b) ascertaining the presence or absence of antibodies that bind to the granulocytes, erythrocytes or platelets only in the presence of the drug, the presence of such antibodies indicating cytopenia mediated by said drug.

In a preferred embodiment, the drug-dependent antibody binding is ascertained by flow cytometry. In another preferred embodiment, wherein the drug is sparingly soluble in water, a solubilizing agent for the drug, e.g., albumin or dimethyl sulfoxide DMSO, is used.

In another preferred embodiment, the drug suspected of inducing cytopenias is present during all or part of the process of ascertaining the presence or absence of the drug-dependent antibodies, whereby the sensitivity of the assay is optimized.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from a careful reading of the disclosure.

BRIEF DESCRIPTION OF THE DRAWINGS

The present invention may be more fully understood by reference to the figures.

FIG. 1 is a group of flow cytometry histograms demonstrating detection of platelet-reactive antibodies stimulated by phenytoin. Histograms are the controls, where histogram/A shows the amount of platelet-bound IgG, Immunoglobulin as indicated by mean platelet immunofluorescence, in the presence of patient serum and phenytoin dissolved in buffer overnight; histogram/B represents the amount of platelet-bound IgG in the presence of normal serum and phenytoin dissolved in 5% bovine serum albumin BSA; and histogram/C represents the amount of platelet-bound IgG in the presence of patient serum and 5% BSA. Histogram/D shows the amount of platelet bound IgG in the presence of patient serum and phenytoin dissolved in 5% BSA.

DETAILED DESCRIPTION

Figure 2A:
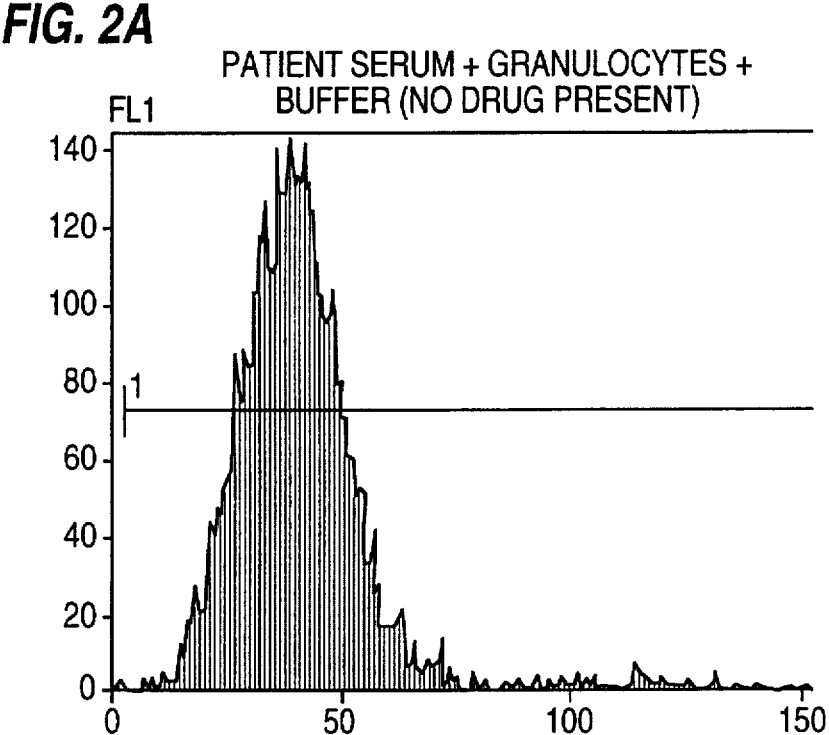
FIG. 2 is a group of flow cytometry histograms demonstrating detection of granulocyte-reactive antibodies stimulated by quinine. Histogram 3A shows the amount of granulocyte bound IgG, in the presence of patient serum without drug; histogram 2B represents the amount of granulocyte bound IgG in the presence of patient serum and 0.2 mM quinine.
Figure 2B:
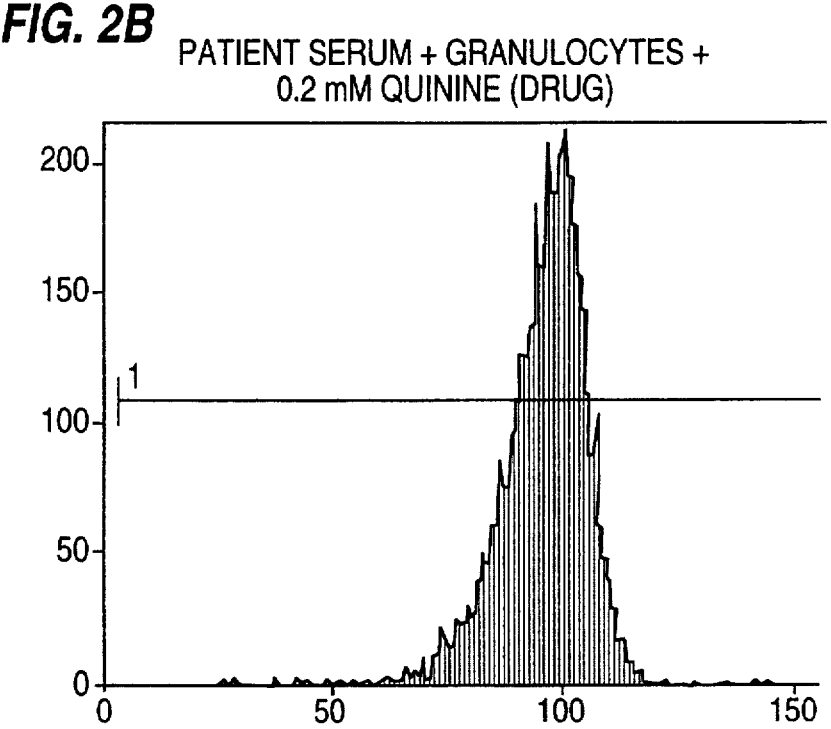

Of the various assays that have been employed to detect drug-dependent antibodies reactive with granulocytes, erythrocytes or platelets, only a few have been successful in recognizing DDAb from amongst the more than 100 different medications implicated in drug induced cytopenia. In general, antibodies induced by quinidine and quinine have been detected by many different methods, whereas antibodies induced by other drugs were very difficult or impossible to identify until now.

The method of the present invention provides a means for detecting drug-dependent antibody binding to granulocytes, erythrocytes and platelets by a variety of assay techniques. For the purposes of discussion, the binding of drug and DDAb to a human blood cell or platelet will be called a drug-antibody-blood cell or platelet complex (hereinafter, complex). The assay of the present invention involves three major elements: (1) the detection of complex formation, (2) the target human blood cells or platelets, and (3) the specific drug implicated in the pathogenesis of the cytopenia.

1. Detection Methods

The method of the present invention may employ a variety of means for detecting the formation of a drug-dependent antibody complex. Methods include the detection of antibody bound to granulocytes, erythrocytes or platelets using a secondary antibody that binds to human immunoglobulin, although other molecules that bind to human Ig, or are activated by human IgG, e.g., complement proteins, staphylococcal protein A, and the like, can also be used.

Means for detecting secondary antibody that binds to the complex include many different labels and methods of labeling known to those of ordinary skill in the art. Examples of the types of labels which can be used in the present invention include enzymes, radioisotopes, fluorescent compounds, colorimetric or enzymatic markers, chemiluminescent compounds, and bioluminescent compounds. Those of ordinary skill in the art will know of other suitable labels for detection of antibody bound to cells or membrane proteins, or will be able to ascertain such using routine experimentation. For example, the secondary antibody may employ such detectable markers as: (a) a fluorescently labeled marker that can be detected or measured by a variety of means, such as standard fluorescence microscopy or flow cytometry (b) a radioactively labeled antibody, which can be detected by means well known to the art, including scintillation counting, and (c) a substrate marker that can provide a colorimetric reaction that can be measured by such means as spectrophotometry or colorimetry.

Labeled secondary antibody may be any antibody, antibody fragment or equivalent antigen-binding molecule that recognizes human Ig, preferably anti-human-Fc-Ig. Labeled secondary antibody, such as anti-human-Fc-Ig, may recognize either IgG, IgM, or IgA, or recognize any combination of such globulin isotypes. Examples of such labeled anti-human-Fc-Ig useful for the detection of antibody bound to cells include, but are not limited to: a labelled anti-human-Fc that is an Ig-F(ab')$_2$ or Ig-Fab.

Furthermore, the binding of these labels to the secondary antibody of the invention can be done using standard techniques common to those of ordinary skill in the art. Examples of such labeled anti-human-Fc-Ig useful for the detection of antibody bound to cells include, but is not limited to: fluorescein [FITC]-labeled anti-human IgG [Fc] F(ab')$_2$ or phycoerythrin-conjugated anti-human IgM [Fc] F(ab')$_2$ or alkaline phosphatase labeled IgG. Radioactively labeled secondary antibodies of the present invention are commercially available or produced according to well-known methods in the art. The binding of a radioactively labeled antibody can be measured by methods well known in the art, such as scintillation counting.

Colorimetric markers include secondary antibody labeled with an enzyme that can catalyze a reaction with a substrate to elicit a colored product. Typically, an enzyme such as alkaline phosphatase is conjugated to anti-human Ig. The amount of bound labeled secondary antibody is measured by adding substrate solution, such as p-nitrophenyl phosphate for the alkaline phosphatase, and measuring the resulting color in a spectrophotometer.

If a fluorescently labeled second antibody is used, it is allowed to incubate in the dark at temperatures and times which allow the binding of secondary antibody to primary antibody; one preferred embodiment being an incubation at room temperature for between 5 and 60 minutes. After incubation with labeled antibody, the cells or platelets are washed and resuspended in PBS-albumin or PBS-DMSO, after which fluorescence is measured.

2. Target Human Blood Cells or Membrane Proteins Derived from Human Blood Cells

The target cells for which drug-dependent antibody binding can be detected employing the method of the present invention include: neutrophils, erythrocytes and platelets. The blood cells and platelets can be prepared by methods well known to those of skill in the art. Also, membrane proteins derived from neutrophils, erythrocytes and platelets can be prepared by methods well known to those of skill in the art.

For platelet preparation, platelet-rich plasma is isolated from blood that has been anticoagulated. Platelets may be aliquoted and frozen, preferably in 5% DMSO, for later use or used immediately. Granulocytes are prepared from anticoagulated normal blood samples by sedimentation of red cells, followed by gradient centrifugation of the leucocyte rich supernatant. The granulocytes may be fixed for later use or used immediately. Red blood cells are isolated from anticoagulated normal blood samples.

Membrane proteins derived from granulocytes, erythrocytes or platelets may be used in the assay of the present invention. Specific relevant target proteins may be isolated from detergent-solubilized platelets, granulocytes or erythrocytes by immunoprecipitation or immobilization using monoclonal antibodies specific for the relevant target protein. For example, the GPIb/IX or GPIIb/IIIa complex from detergent-solubilized platelets may be captured by microtiter plate-immobilized monoclonal antibodies specific for such membrane proteins. See Visentin, et al., *Transfusion* 30: 694 (1990), the contents of which are incorporated herein by reference in their entirety. Alternatively, membrane preparations from granulocytes, erythrocytes or platelets may be prepared by methods well known to those of skill in the art. One example of a membrane preparation is the sonication or homogenization of a human blood cell suspension, followed by centrifugation at 12,000×gravity to isolate the human blood cell membrane preparation containing the cell membrane proteins. Membrane preparations containing the cell membrane proteins may be frozen for use in later assays.

3. Drugs Tested for Involvement in Drug-dependent Antibody Binding to Blood Cells or Platelets.

The prior art failed to detect the drug-dependency of antibody binding in many cytopenias. For purposes of this disclosure, the term "drug" will include, in additional to medicaments, environmental pollutants and foods that cause cytopenia. The prior art failed to recognize a crucial aspect of assaying the formation of drug-antibody-blood cell or platelet complex, specifically that drug solubility is an important factor in the formation of such complexes. The present invention avoids the prior art unrecognized problem of drug solubility in the formation of detectable complex by employing a variety of means to ensure that the implicated drug is available to form the complex.

The method of the present invention employs a variety of means which permit the drug to dissolve in water and maintain the drug in solution. The method of the present invention can be performed using drug that has been solubilized by such means as: (1) overnight dissolution; or (2) use of such solubilizing agents as albumin or dimethyl sulfoxide (DMSO). A solubilizing agent is any compound that permits a drug to dissolve in water and which maintains the drug in solution. Such a solubilizing agent is used in an effective amount which is any amount that solubilizes the drug and maintains the drug in solution. Solubilizing agents may act as a carrier that binds to the drug to maintain the drug in solution and available for blood cell, platelet and antibody binding.

Another aspect of the present invention is the recognition of which assay steps should be effected in the presence of the drug and/or the solubilizing agent. In one preferred embodiment of the invention the solubilizing agent is present in the primary binding incubation, where patient serum is bound to platelets or blood cells in the presence of drug, as well as the secondary detection steps and intermediate washes. In another preferred embodiment, the drug and solubilizing agent are present in all assay steps up to the binding of the detectable secondary antibody. Thereafter, in general, neither drug or solubilizing agent are needed for complex detection.

The inability in the prior art to detect DDAbs with greater frequency in patients with drug-induced cytopenia was probably due to on or more of the following factors: (1) the insensitivity of available assays; (2) the relative insolubility in water of many of the drugs that cause drug dependent cytopenia; and (3) the high backgrounds obtained when excessive concentrations of insoluble drugs, or drugs dissolved in organic solvents such as methanol or ethanol, were employed in the prior art assays. Drugs that are not very soluble in either water or buffer will be referred to as "sparingly soluble in water". Sparingly soluble drugs mean drugs whose solubility in water is less than 0.1 mg/ml. Examples of sparingly soluble drugs that cause cytopenia include: diclofenac, Fenoprofen, Ibuprofen, Indomethacin, Naproxen, Phenylbutazone, Piroxicam, Tolmetin, Fluconazole, Nalidizic acid, Norfloxacin, Spiramycin, Trimethoprim, Sulfasalazine, sulfamethizole, sulfanilamide, sulfamerazine, sulfadimethoxine, Chlorpropamide, Diazoxide, Furosemide, Carbamazepine, Diazepam, Phenytoin, Chlorothiazide, Danazol, Digitalis, Digitoxin, Digoxin, Diltiazem, Etretinate, Furosemide, Hydrochlorothiazide, methylchlorothiazide, Isotretinoin, Levodopa, Nifedipine, Spironolactone, tolbutamide, probenecid, triamterene, 5-fluorouracil, sulindac, pentazocine, sulfamethooxazole, dapsone, acetazolamide, chlorthalidone, tolbutamide, clozapine, diazepam and.

Identification of the drug responsible for a patient's drug-induced cytopenia is often difficult when the patient is taking multiple drugs or when the patient has a disorder that is complicated by cytopenia. It is important to identify the drug that is causing the cytopenia so that its administration can be stopped and the patient can avoid the morbidity and, occasional mortality associated with this condition.

The method of the present invention provides an extremely sensitive method for detecting very low serum titers of drug-dependent antibodies that bind to GEP or membrane proteins isolated from GEP. Using very low concentrations of drug (as low as 0.1 µM) and/or very low antibody titers (as low as 1:1000), complex formation can be detected. At the concentrations of drug used in the method of the present invention, the drug alone does not affect fluorescence values, as shown by the results obtained when the method of the present invention uses normal serum.

The method of the present invention employs a reaction between blood cells or platelets and patient serum in the presence of drug. Granulocytes, erythrocytes or platelets are reacted with each of the following: (i) a serum or plasma sample derived from a patient suspected of having a drug-dependent antibody-mediated cytopenia, and (ii) a drug suspected of causing the cytopenia.

The patient's serum or plasma is reacted with either a granulocyte sample, erythrocyte sample or platelet sample obtained by the methods well known to the art, such as those described in Example 1. Controls consist of: (1) reaction mixtures that contain patient serum without drug, (2) reaction mixtures that contain normal serum with drug and (3) reaction mixtures that contain normal serum without drug.

When a patient's serum is tested for antibodies that bind GEPs in the presence of a sparingly soluble drug, the drug is dissolved in buffer overnight or a buffer containing a solubilizing agent. Examples of preferred solubilizing agents include albumin or dimethyl sulfoxide (DMSO). The controls employed when such a sparingly soluble drug is tested include: (1) normal serum plus buffer containing a solubilizing agent such as albumin or DMSO and (2) normal serum plus drug dissolved in a solubilizing agent such as albumin or DMSO.

Examples of albumin for use in the present invention include: ovalbumin, bovine serum albumin, equine serum albumin, ovine serum albumin, porcine serum albumin, subhuman primate serum albumin and human serum albumin.

The reaction mixture is incubated to form a drug-antibody-blood cell or platelet complex with any DDAbs present in the patient sample. The temperature and time required for complex formation are those that permit drug-antibody-platelet complex formation; such incubation times and temperatures can be determined easily by one of ordinary skill in the art. Preferably, the incubation is performed at room temperature for a time period between 5 and 60 minutes.

The reacted human blood cells or platelets are washed with a wash solution. Any wash solution may be employed which does not disassociate formed complex. Some preferred wash solutions include buffer containing between 0.1% to 5% albumin or 0.1% to 5% DMSO and suspected drug. After the wash, the cells or platelets are resuspended in labeled secondary antibody.

In one preferred embodiment of the invention, drug is present during some or all assay steps in order to maximize the sensitivity of the test. In another preferred embodiment of the invention, drug is present both in the primary mixture and in the subsequent washing steps to achieve maximum sensitivity. In yet another embodiment of the invention, drug is present in the primary mixture, subsequent washing steps, and secondary labeled anti-immunoglobulin incubation to achieve maximum sensitivity. Although drug need not be present in washes carried out after addition of the labeled anti-immunoglobulin, drug may be present to achieve the same sensitivity. To the extent that a solubilizing agent is necessary or desirable to maintain a drug in solution, an effective amount of a solubilizing agent will also be present in those steps where drug is present. When drugs that are sparingly soluble in water are being tested for DDAb binding to blood cells or platelets, one preferred embodiment of the invention is the inclusion of a solubilizing agent, such as albumin or DMSO whenever drug is present in the assay in order to achieve maximum sensitivity.

If drug concentration decreases, fluorescence drops off significantly. Adequate concentrations of drug can readily be achieved using a solubilizing agent, such as albumin or DMSO, to facilitate maintenance of drug in solution in an aqueous medium. For each of these steps, the range of concentration of drug necessary for detection can be determined easily. The drug concentrations required for DDAb binding are usually between 0.1 mM and 1 mM.

When detecting antibodies that bind cells or platelets in the presence of a sparingly soluble drug, the range of concentration of albumin or DMSO needed in each of the steps can be determined easily. The albumin or DMSO concentrations must be adequate to maintain the sparingly or insoluble drug in solution. Roughly, there must be at least one molecule of drug for each molecule of albumin. For example, for 0.1 mM of drug, 0.1 mM or 0.7% albumin is required for drug solubility, for 0.2 mM of drug, 0.2 mM or 1.4% albumin is required for drug solubility, etc.

THROMBOCYTOPENIA

Drug-dependent antibodies have been identified for only a few of the numerous medicaments implicated in mediating drug-induced thrombocytopenia. The .drugs that have been shown to mediate antibody binding to platelets in the pathogenesis of thrombocytopenia include: quinine, quinidine, acetaminophen, acetaminophen metabolites, Cefotetan, diphenylhydantoin, diazepam, novobiocin, penicillin, rifampin, vancomycin, valproic acid, cyanidanol, procainamide, sulfisoxazole, sulfamethoxazole, sulfamethoxazole metabolites, Para-aminosalicylic Acid (PAS), PAS metabolites and stibophen. Kelton et al., *Blood* 58:524 (1981); Cimo, et al., *Am. J. Hematol.* 2: 65 (1977); Hamilton et al., *JAMA* 239: 2586 (1978); Visentin et al., *Transfusion* 30:694 (1990); Kieffel, et al., *Transfusion* 27:262 (1987); Aster et al., supra; Christie et al., *J. Clin. Invest* 75: 310 (1985); Smith et al., *J. Clin. Invest.* 79: 912 (1987); Christie et al., *Br. J. Haematol.* 67: 213 (1987); Eisner et al., *N. Engl. J. Med.* 287: 376 (1972); Shoenfeld et al., *N. Engl. J. Med.* 303: 47 (1980); Christie et al., *Transfusion* 28: 322 (1988); Day et al., *Am. J. Med. Sci.* 236: 475 (1958); Conti et al., *Haemostasis* 14: 480 (1984); Kakaiya et al., *Vox. Sang.* 57: 185 (1989); Christie et al., *Blood* 75: 518 (1990); Zenon et al., *Arch. Intern. Med.* 151: 995 (1991); Barr et al., *Arch. Dis. Child* 57: 681 (1982); Gandolfo et al., *Acta Haematologica* 88: 96 (1992); Gafter et al., *Ann. Intern. Med.* 106: 477 (1987); Kahn et al., Arch. Intern. Med. 108: 496 (1961). Bajjoka *Arch. Intern. Med.* 151: 203 (1991); Kelton et al., *Blood* 58: 524 (1981); Cimo, supra; Visentin et al., supra; Kieffel, supra and Aster et al., supra.

Methods for detecting drug-dependent antibodies that react with platelets include: platelet aggregation/agglutination, serotonin release, platelet factor III availability, clot retraction inhibition, platelet migration inhibition, complement fixation and platelet lysis. Hackett et al., *Semin. Thromb. Hemostas.* 8: 116 (1982); Karpatkin *Amer. J. Med. Sci.* 262: 68 (1971). Because of the insensitivity of these assays, they are not recommended for the diagnosis of typical drug-induced immune thrombocytopenia (DITP). Chong, *Platelets* 2: 173 (1991). More sensitive tests for detecting drug-dependent platelet-reactive antibodies include: direct or indirect measurement of immunoglobulin bound to platelets. Hackett et al., *Semin. Thromb. Hemostas.*, supra. $^{51}$Cr-platelet lysis (Cimo, supra), antigen capture ELISA (Visentin, et al., supra); Kunicki et al., *Transfus. Med. Rev.* 1: 21 (1987)) and platelet-antibody ELISA (Savoca U.S. Pat. No. 4,717,654).

Even using these more sensitive methods, the presence of DDAbs have only been confirmed in a small fraction of patients suspected of having drug induced thrombocytopenia. In particular, DDAbs induced by quinine, quinidine (Kelton et al., *Blood* 58:524 (1981); diphenylhydantoin, diazepam, and sulfisoxazole (Cimo, supra); sulfamethoxazole (Visentin et al., *Transfusion* 30:694 (1990)) and metabolites of trimethoprinsulfamethoxazole (Kieffel, et al., *Transfusion* 27:262 (1987) have been detected.

However, serological assessment is still fraught with false negative results, so that the presence of DDAbs and incidence of these reactions cannot be estimated accurately. Salama et al., *Semin. Hematol.*, supra.

Drugs and other agents that have been implicated, yet not heretofore detected as causing antibody dependent drug-induced thrombocytopenia include: (A) Analgesics: Antipyrine, benoxaprofen, diclofenac, Fenoprofen, Ibuprofen, Indomethacin, Meclofenamate, Naproxen, Nimesulfide, Noramiopyrine, Oxyphenbutazone, Phenylbutazone, Piroxicam, Sodium salicylate, Sulindac, Tolmetin; (B) Antimicrobials: Amphotericin B, Ampicillin, Apalcillin, Carbenicillin, Cefotetan, Ceftazidine, Ceftriaxone, Cephalexin, Cephalothin, Cephamandole, Clarithromycin, Cloxacillin, Didanosine (ddI), Difluoromethylornithine, Ethambutol, Fluconazole, Fusidic acid, Gentamicin, Hydroxychloroquine, Isoniazid, Lincomycin, Methicillin, Mezlocillin, Moxalactam, Nalidizic acid, Nitrofurantoin, Norfloxacin, Novobiocin, Oxytetracycline, p-Aminosalicylate, Penicillin, Pentamidine, Piperacillin, Rifampin, Spiramycin, Stibogluconate, Streptomycin, Tobramycin, Trimethoprim, Vancomycin, Sulfasalazine, N-acetylsulfanilamide sodium; succinylsufathiazole, phthalysulfathizole, sulfaguanidine, sulfamethizole, sulfanilamide, sulfamerazine, sulfathiazole, sulfadimethoxine, sulfamethoxypyridazine; Acetazolamide, Chlorpropamide, Chlorthalidone, Clopamide, Diazoxide, Furosemide, Glibenclamide, Glymidine, Methazolamide, Tolbutamide; (C) Sedatives/Tranquilizers/Anticonvulsants: Allylisopropylacetylurea, Allylisopropylbarbiturate, Butabarbitone, Carbamazepine, Centalun, Chlordiazepoxide, Chlorpromazine, Clonazepam, Diazepam, Fluphenazine, Haloperidol, Imipramine, Meprobamate, Methotrimeprazine, Mianserin, Paramethadione, Phenytoin, Phthalazinol, Primidone, Valproic acid; (D); (E) Others: Actinomycin, Allopurinol, Alpha methyldopa, L-dopa Aminoglutethimide, Amiodarone, Amrinon, Antazoline, Bleomycin, Butoconazole cream, Captopril, Chenodeoxycholic acid, Chloroquine, Chlorothiazide, Chlorpheniramine, Cimetidine, Clometacine, Cocaine, Cyclophosphamide, Cyclosporine A, Danazol, Desferrioxamine, Diatrizoate, Digitalis, Digitoxin, Digoxin, Diltiazem, Disulfiram, Doxepin, Etretinate, Famotidine, Flavone-8-acetic acid, Heroin, Hydrochlorothiazide, methylchlorothiazide, Hydroxyquinoline, Iocetamic acid, Iopanoic acid, Interferon, Isotretinoin (vitamin A), Levamisole, Levodopa, Lidocaine, Lithium carbonate, Lithium citrate, Thiomerazol, Methylphenidate, Mexiletine, Minoxidil, Morphine, Nifedipine, Nitroglycerin, Nomifensine, Octreotide acetate, Odansetron, Oxprenolol, Penicillamine, Pentagastrin, Pentosane polysulfate, Pertussis vaccine, Piperazine, Plicamycin, Polyurethane, Procainamide, Prochlorperazine, Propranolol, Propylthiouracil, Simvastatin, Spironolactone, Suramin, Thioguanin, Thiouracil, Ticlopidine, Tienilic acid, Toluene diisocyanate, Vinyl chloride. Aster et al., supra.

The method of the present invention is capable of detecting the above recited drugs involved in drug-dependent antibody binding to human platelets. For example, the prior art was unable to detect antibody binding in a granulocytopenic patient who had been taking phenytoin. Sharafuddin et al. supra. However, the assay of the present invention is capable of detecting phenytoin-dependent antibody binding to granulocytes, erythrocytes or platelets.

Among the above recited drugs, for example, the thiazide group of diuretics, including chlorothiazide, hydrochlorothiazide and methylchlorothiazide, produce thrombocytopenia in 1–2% of patients who receive those drugs. Dinon et al., Am. J. Med. Sci. 236: 533 (1959); Nordvist et al., Lancet 1: 271 (1959); Bottinger, L. E. et al., Acta Med. Scand. 191: 541 (1972); Kutti et al., Acta Med. Scand. 183: 245 (1968). Serologic tests for drug antibodies in thiazide-induced thrombocytopenia have been either negative or inconsistent for heart disease patients taking thiazide and newborn thrombocytopenia due to mothers who took thiazide during pregnancy. Rodriguez et al., *New Engl. J. Med.* 270: 881 (1964); Bettman, *Arch. Intern. Med.* 112:840 (1963). The method of the present invention is capable of identifying thiazide-dependent antibody binding to platelets.

GRANULOCYTOPENIA

More than 100 different medications have been implicated in the pathogenesis of drug-induced neutropenia or granulocytopenia. The prior art method for detecting drug induced neutropenia or granulocytopenia are limited to: (a) leukagglutination, which measures granulocyte lysis on addition of plasma or serum from drug associated agranulocytosis; Moeschlin et al., *Acta Hematologica* 8: 29 (1952); (b) immunofluorescence, which detects antibody binding to granulocytes in the presence or absence of offending drug; Murphy et al. *Br. J. Haemat.* 59: 9 (1985); Stroncek et al., *Blood* 81: 2758 (1993); Verheugt et al., *Br. J. Haemat.* 36: 533 (1977); and (c) Nitroblue tetrazolium (NBTZ) reduction, which measures glucose oxidation elicited by the opsonization of neutrophils by anti-neutrophil antibodies present in a patient's serum; Weitzman et al., *Lancet* 1: 1068 (1978).

Drugs and other agents that have been implicated, yet not heretofore detected in the available assays as causing drug-dependent antibody-binding to granulocytes or neutrophils include: (A) Analgesics and anti-inflammatory agents: noramidopyrine, metamizole, indomethacin, gold salts, pentazocine, para-aminophenol derivatives such as acetaminophen and phenacetin, pyrazolone derivatives such as aminopyrine, dipyrone, oxyphenbutazone and phenylbutazone; (B) Antibiotics: cephalosporins, chloramphenicol, clindamycin, gentamicin, isoniazid, para-aminosalicylic acid, penicillin, rifampin, streptomycin, sulfonamides, tetracycline, trimethoprinsulfamethoxazole, vancomycin; (C) Anticonvulsants: carbamazepine, mephenytoin, phenytoin,; (D) Antidepressants: amitriptyline, amoxapine, desipramine, doxepin, imipramine; (E) Antihistamines: cimetidine, ranitidine; (F) Antimalarial: chloroquine, dapsone, pyrimethamine; (G) Antithyroid drugs: carbimazole, methimazole, proylthiouracil; (H) Cardiovascular drugs: ticlopidine, captopril, disopyramide, hydralazine, methyldopa, procainamide, propranolol, quinidine, tocainide; (I) Diuretics: acetazolamide, chlorthalidone, chlorothiazide, ethacrynic acid, hydrochlorothiazide; (J) Hypoglycemic agents: chlordiazepoxide and tolbutamide; (K) Hypnotics and sedatives: clozapine, chlordiazepoxide and other benzodiazepines, meprobamate; (L) Phenothiazines: chlorpromazine and phenothiazines and (M) such other drugs as allopurinol, levamisole and penicillamine.

In the case of clozapine induced granulocytopenia, 1.3% of all patients taking the drug develop granulocytopenia. Therefore patients taking clozapine have a significant risk of developing granulocytopenia and are required to be monitored by weekly blood tests for the occurrence of agranulocytosis. PHYSICIANS' DESK REFERENCE (Medical Economics Data, Montvale, N.J. 1993) The prior art was unable to detect clozapine-dependent antibodies in serum of patients with clozapine-induced granulocytopenia. Pisciotta et al., supra. The method of the present invention is capable of detecting clozapine-dependent antibodies in serum of patients with clozapine-induced granulocytopenia. Potentially, the method of the present invention can be used to detect clozapine-dependent antibodies in patients taking clozapine prior to a significant decrease in the patient's granulocyte count.

In the case of ticlopidine induced neutropenia, 0.8% of patients taking this drug develop severe neutropenia and/or agranulocytosis (i.e. less than 450 neutrophils/mm$^3$) and 1.6% of the patients on this drug develop mild to moderate neutropenia (i.e. between 451 and 1200 neutrophils/mm$^3$). PHYSICIANS' DESK REFERENCE (Medical Economics Data, Montvale, N.J., 1993) Therefore patients taking ticlopidine have a significant risk of developing neutropenia, which results in an increased risk of infection. Patients taking ticlopidine to help reduce their risk of having a stroke, must have their blood tested every two weeks for the first three months on the medication. The prior art was unable to detect clozapine-dependent antibodies in serum of patients with ticlopidine-induced granulocytopenia. Ono et al., *Am J. Hematol.* 37: 239 (1991). The method of the present invention is capable of detecting ticlopidine-dependent antibodies in serum of patients with ticlopidine-induced neutropenia. Potentially, the method of the present invention can be used to detect ticlopidine-dependent antibodies in patients taking ticlopidine prior to a significant decrease in the patient's neutrophil count.

The drugs for which drug-dependent antibody binding to human granulocytes has been detected include: quinine and quinidine (Stroncek et al., supra), penicillin (Salama et al., *Br. J. Haematol.* 72: 127 (1989)), the semisynthetic penicillin Nafcillin and Oxacillin (Weitzman et al., supra) propylthiouracil (Fibbe et al., *Br. J. Haematol.* 64: 363 (1986)), propyphenazone (Salama et al., supra); and amodiaquine (Rouveix et al., *Br. J. Haematol.* 71: 7 (1989).

HEMOLYTIC ANEMIA

A number of medications have been implicated in the pathogenesis of drug-induced hemolytic anemia. The prior art method for detecting drug-induced hemolytic anemia is limited to the direct "Coombs test" or antiglobulin test. Packman et al., in Williams et al. (eds.) HEMATOLOGY (4th edition, McGraw Hill, 1990) Chapter 69. The direct Coombs tests for the presence of drug-dependent RBC specific antibodies present in a patient's serum by incubating donor erythrocytes with patient serum and drug. Anti-human globulin is added to the reaction, after which agglutination indicates that the presence of drug-dependent antibodies in the patient's serum. Petz et al., *Transfusion* 32: 202 (1992); Garratty et al., *Am. J. Med* 58: 398 (1975); Salama et al., *Br. J. Haematol.* 78: 535 (1991).

Drugs and other agents that have been implicated, yet not heretofore detected using the available assays as causing drug-dependent antibody-binding to erythrocytes include: tetracycline, carbromal, tolbutamide, chlorpropamide, antazoline, thiopental, tolmetin, probenecid, mesantoin, phenacetin, insecticides, chlorpromazine, melphalan, isoniazid, p-aminosalicylic acid, acetaminophen, thiazides, streptomycin, ibuprofen, triamterene, erythromycin, 5-fluorouracil, nalidixic acid, sulindac, sulfonylurea, warfarin, propanil, diethylstilbestrol, and insulin. Leddy et al., in Williams et al. (eds.) HEMATOLOGY (4th edition, McGraw Hill, 1990). The method of the present invention is capable of detecting the above recited drugs involved in drug-dependent antibody binding to human erythrocytes.

In reviewing the literature, it is not always possible to be certain that the cited drug is unequivocally involved in the pathogenesis of the hemolytic anemia, let alone responsible for drug-dependent antibody binding to erythrocytes. The drugs for which drug-dependent antibody binding to human erythrocytes have been detected include: quinine and quinidine (Muirhead et al., *Arch. Intern. Med.* 101: 827 (1958); Freedman et al., *Am. J. Med.* 20: 806 (1956), Ceftazidime (Chambers et al., *Am. J. Clin. Pathol.* 95: 393 (1991); diclofenac (Salama et al., *Br. J. Haematol.* 77: 546 (1991) and rifampicin (Lakshminarayan et al., *Br. Med. J.* 2: 282 (1973), cyanidanol (Gandolfo et al., *Acta Haematolog.* 88: 96 (1992), ceftriaxone (Garratty et al., *Transfusion* 31: 176 (1991), cefotetan (Wagner et al., *Ann. Pharacother.* 26: 199 (1992).

METABOLITES

Drug metabolites of the above recited drugs also have been implicated as causing immunologically mediated cytopenia. In many drug-induced immune reactions, metabolites, rather than the native drugs, are the primary immunizing agents. In some patients, the antibody binding to blood cells or platelets may be mediated by metabolite(s) of the drug and not by the drug itself. Kiefel, et al., *Transfusion* 27: 262 (1987). Cases of drug-dependent immune thrombocytopenia have been shown to be caused by both a metabolite of acetaminophen and a metabolite of p-aminosalicylic acid. Eisner, et al., *N. Engl. J. Med.* 287: 376 (1972); Eisner et al., *Am. J. Med.* 53: 790 (1972).

Presently, methods for detecting a drug metabolite as mediating antibody binding to human blood cells or platelets is use of either: (a) urine, urine extracts or serum from a normal person who has ingested the drug of interest or (b) known drug metabolites of the above recited drugs that are available from the manufacturer. Normal urine is used in the control samples for the present invention's method of detecting a drug metabolite as mediating antibody binding to human blood cells or platelets.

The method of the present invention is capable of detecting the metabolites of the above recited drugs involved in drug metabolite-dependent antibody binding to human granulocytes, erythrocytes or platelets or membrane proteins derived from these cells.

In carrying out the assay of this invention, the quantities of materials utilized are not in themselves critical and may be varied within the scope and spirit of the invention. Without further elaboration, it is believed that one skilled in the art can, using the preceding description, utilize the present invention to its fullest extent. The following examples are merely illustrative and not limitative of the remainder of the disclosure in any way whatsoever.

EXAMPLES

EXAMPLE 1

Platelet, Red Blood Cell and Granulocyte Preparation

For platelet preparation, platelet-rich plasma is isolated from blood that has been anticoagulated. Typical anticoagulants for use in the present invention include, but are not limited to acid-citrate-dextrose-A anticoagulant (ACD-A) anticoagulant and EDTA. Platelets may be aliquoted and frozen in 5% DMSO at −80° C. for later use or used immediately. If frozen, platelets are thawed at 37° C. Before use, platelets are washed three times in buffer. Buffer may be either (a) 0.027M phosphate-buffered isotonic saline, about pH 7.1 to 7.4, containing 9 mM EDTA and between 0.1% and 5% bovine serum albumin or between 0.1% and 5% DMSO in PBS or Ringers-citrate-dextrose (RCD) buffer. The platelets are used at a final concentration of between $5 \times 10^4$ per µl and $1 \times 10^7$ per µl, preferably between $1.0 \times 10^5$ per µl and $3.0 \times 10^5$ per µl, and most preferably at $3.0 \times 10^5$ per µl.

Granulocytes are prepared from EDTA treated normal blood samples by dextran sedimentation of red cells, followed by Ficoll-hypaque gradient centrifugation of the leucocyte rich supernatant. Granulocytes are washed three times in PBS. The granulocytes may be fixed for 5 minutes at 20° C. with 1% (w/v) paraformaldehyde in PBS.

Red blood cells are prepared from EDTA treated normal blood samples by centrifugation to obtain red blood cell rich pellet. The red blood cells are washed three times in buffer to remove any serum.

EXAMPLE 2

Fluorescent Detection of Sparingly Soluble Drug

The detection of platelet-reactive antibodies which depend on the presence of a sparingly soluble drug can be shown employing the assay of the present invention. Each of the drugs phenytoin, carbamazepine, sulfisoxazole, sulfamethoxazole and trimethoprim are insoluble or poorly soluble in water. Each of these drug is dissolved in bovine serum albumin (BSA) and mixed with serum obtained from thrombocytopenic patients who were taking the indicated drug. Typically, serum from a patient (60 ul) is incubated with $2.5 \times 10^7$ normal platelets in the presence and absence of drug in 1% albumin. After washes in buffer containing drug at the same concentration as in the primary mixture, platelet-bound immunoglobulin is detected with fluorescein-labeled anti-IgG Fc.

EXAMPLE 3

Flow Cytometry

Target cell or platelet-bound fluorescent label is analyzed by flow cytometry and mean fluorescence intensity is determined. The calibration of a flow cytometer for the various GEP target cells or membrane preparations from such cells is well known to those of skill in the art.

Controls consist of patient serum without drug and normal serum with and without drug. Mean fluorescence intensity obtained with a patient's serum in the presence of an implicated drug was divided by fluorescence intensity without drug, and this ratio is used as an index of drug-dependent deposition of immunoglobulin on the target platelets. Normal sera tested with and without drug yielded an average ratio of 0.97±0.03 (standard deviation) relative to a normal reference standard. At the concentration of drug used in these studies, the drug alone did not affect fluorescence values, as shown by the results obtained with normal serum. Patient sera yielding a ratio of 1.5 or greater is considered to be positive for drug-dependent, platelet-reactive antibody.

The reaction mixture is incubated for about 15 to about 60 minutes at room temperature to form a drug-antibody-blood cell or platelet complex with any DDAbs present in the patient sample. The reacted cells or platelets are washed three times with a wash solution containing between 0.1% to 5% albumin or 0.1% to 5% DMSO and suspected drug. After the wash, the cells or platelets are resuspended in labeled secondary antibody.

Labelled secondary antibody may be any antibody that recognizes human Ig, preferably anti-human-Fc-Ig. Labeled anti-human-Fc-Ig may recognize either IgG, IgM, or IgA, or recognize any combination of such globulin isotypes. Examples of such labeled anti-human-Fc-Ig useful for the detection of antibody bound to cells include, but are not limited to: a labelled anti-human-Fc that is an Ig-F(ab')$_2$ or Fab. The label on the anti-human-Fc-Ig may be any mechanically or visibly detectable marker, such as a fluorescent marker, colorimetric marker or a radioactive marker. Examples of such labeled anti-human-Fc-Ig useful for the detection of antibody bound to cells include, but is not limited to: fluorescein [FITC]-labeled anti-human IgG [Fc] F(ab')$_2$, phycoerythrin-conjugated anti-human IgM (Fc] F(ab')$_2$, and anti-human IgG conjugated alkaline phosphatase.

Samples are analyzed on a flow cytometer equipped with a 5-watt argon ion laser. Fluorescein fluorescence was detected through a 530±nm band-pass filter. Logarithmic amplification for the fluorescence signal is used to calibrate the fluorescence [and size for other cytopenias]. Fluorescent histograms are drawn from 10,000 ungated events. The data is analyzed using a software program (Lysys, Becton Dickinson).

The presence of drug-dependent antibody bound to cells or platelets is ascertained by dividing (i) the mean fluorescence intensity of the cells or platelets with patient's serum in the presence of implicated drug by (ii) the mean fluorescence intensity of the cells or platelets with patient's serum in the absence of implicated drug, to obtain a mean fluorescence ratio. A ratio of about 1.5 or greater, preferably about 2.0 or greater, indicates the presence of drug-dependent antibodies in the patient sample.

The fluorescence intensities of different stained populations can be compared by converting the logarithmic fluorescence channel intensity to arbitrary linear units. For example, a determination that a doubling of fluorescence intensity causes a shift of 19.3 channels on the 256-channel scale serves to convert fluorescence intensities of one population to another.

EXAMPLE 4

The mean platelet immunofluorescence values obtained in studies with drug-induced antibodies are shown in Table 1. The values are the ratios of mean platelet fluorescence obtained with serum plus drug to that obtained with serum in the absence of drug. A value of greater than 1.5 is unequivocally positive, provided that the drug alone does not increase mean platelet fluorescence.

TABLE 1

| SERUM | DRUG Concentration (mg/ml) | Serum without drug | | Serum with drug | |
|---|---|---|---|---|---|
| | | Microplate Ratio | Tube Ratio | Microplate Ratio | Tube Ratio |
| Ja | Phenytoin (0.5) | 1.9 | 1.2 | 3.2 | 3.7 |
| | 0.25 | | | 2.5 | |
| Zw | Trimethoprim (0.5) | 1.4 | 1.6 | 4.1 | 4.1 |
| | 0.25 | | | 3.2 | |
| J. T. | Sulfisoxazole (5.0) | 1.2 | 1.2 | 3.5 | |
| | 2.50 | | | 3.5 | 3.3 |
| | 1.00 | | | 2.9 | |
| Go 1:10 | Carbamazepine (0.5) | 1.0 | 1.0 | 8.1 | 4.9 |
| | 0.25 | | | 7.5 | |
| Na (Abs) | Rifampin (5.0) | 1.1 | 1.3 | 2.7 | |
| | 2.50 | | | | 2.6 |
| | 1.00 | | | 2.7 | 3.0 |
| He | Ranitidine (0.25) | 1.1 | 1.2 | 13.3 | 10.0 |
| Normal Serum | Phenytoin (0.5) | 1.2 | | 1.1 | |
| E2076 | Trimethoprim (0.5) | | | 0.9 | |
| | Carbamazepine (0.5) | | | 0.9 | |
| | Sulfisoxazole (5.0) | | | 0.9 | |
| | Rifampin (5.0) | | | 1.1 | |
| | Ceftriaxone (5.0 | | | 0.7 | |
| | Ranitidine (0.25) | | | 1.1 | |
| | Sulfamethoxazole (2.0) | 1.5 | | 1.0 | |
| | Quinine (0.5) | | | 1.0 | |
| | Quinidine (2.0) | | | 1.0 | |
| | Vancomycin (5.0) | 1.2 | | 1.1 | |
| Cl 1:30 | Sulfamethoxazole (2.0) | 1.3 | | 16.0 | 16.6 |
| Bu | Sulfamethoxazole (8.0 | 1.8 | 1.3 | 6.0 | |
| | 5.00 | | | 5.4 | |
| | 2.00 | | | 5.8 | |
| In | Vancomycin (5.0) | 1.2 | 1.2 | 3.1 | 3.0 |
| | 2.50 | | | 2.5 | |
| | 1.25 | | | 2.8 | |
| Be | Quinine (1.0) | 1.2 | 1.1 | 4.2 | 4.5 |
| | 0.50 | | | 4.1 | |
| We | Quinine (0.5) | 1.6 | 1.5 | 4.1 | 4.1 |
| Si 1:10 | Quinidine (0.5) | 1.2 | | 2.8 | |
| | 2.00 | | | 4.1 | |
| Ar 1:20 | Quinidine (2.0) | 1.2 | | 13.3 | |
| Si 1:5 | Quinidine (2.0) | 1.0 | 1.1 | 6.5 | 6.5 |
| Ch | Ceftriaxone (5.0) | 1.2 | 1.3 | 2.6 | |
| | 2.50 | | | 2.4 | |
| | 1.00 | | | 2.6 | 3.0 |

EXAMPLE 5

Phenytoin-dependent Antibodies

A comparison of the assay of the present invention performed using phenytoin dissolved overnight with the assay of the present invention performed using BSA solubilized phenytoin, as shown in FIGS. 1A and 1D, respectively, revealed that phenytoin must be dissolved in albumin in order for phenytoin-dependent platelet-reactive antibodies to be detected in a patient's serum. Thus, phenytoin must be suspended in albumin in order to detect DDAbs that bind GEP and require phenytoin.

EXAMPLE 6

Effect of Drug in Wash Steps

Figure 3A:
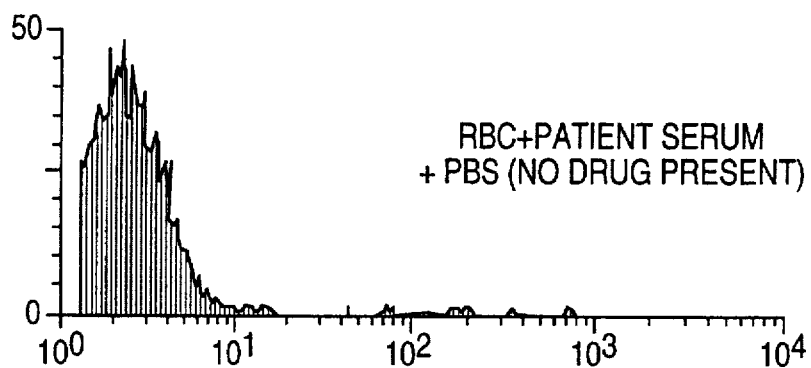
FIG. 3 is a group of flow cytometry histograms demonstrating the detection of Cefotetan-dependent antibodies that bind red blood cells (RBCs). Histogram 3A shows the amount of red blood cell bound IgG, as indicated by mean erythrocyte immunofluorescence in the presence of patient serum and phosphate buffered saline PBS; histogram B represents the amount of red blood cell bound IgG in the presence of patient serum and 1 mM Cefotetan where no drug was present during the washing of the RBCs. Histogram 3C represents the amount of red blood cell bound IgG in the presence of patient serum and 1 mM Cefotetan, where drug was present during the washing of the RBCs.
Figure 3B:
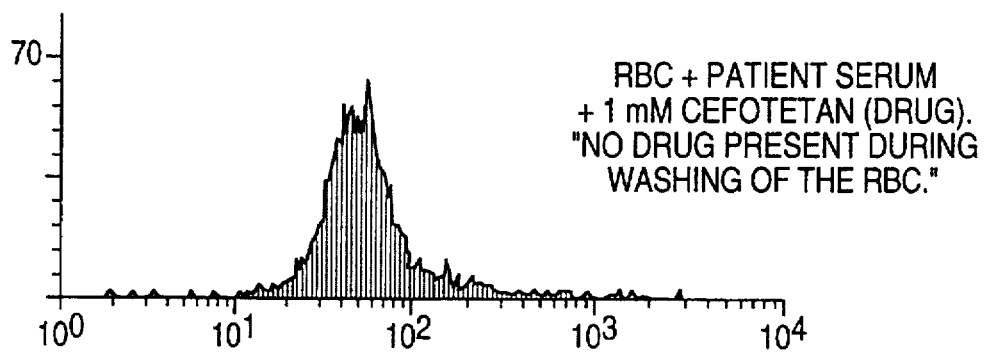
Figure 3C:
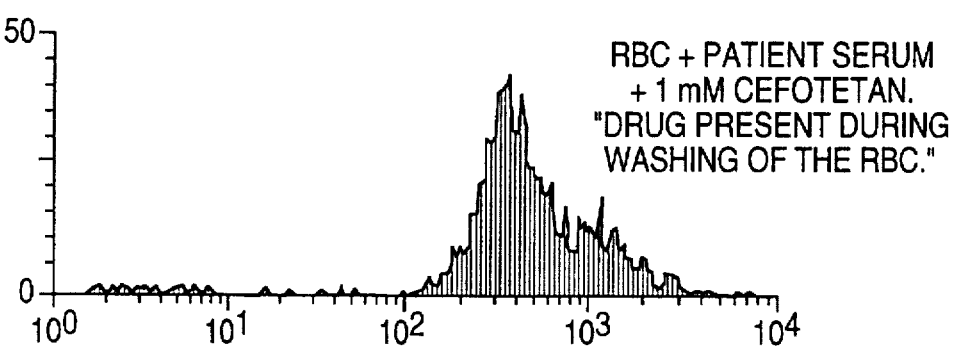

The detection of Cefotetan-dependent antibody binding to RBCs is enhanced when Cefotetan is included in the cell washes. FIG. 3 shows a group of flow cytometry histograms demonstrating the detection of Cefotetan-dependent antibodies that bind red blood cells. Where no drug was present during the washing of the RBCs, the amount of red blood cell bound IgG in the presence of patient serum and 1 mM Cefotetan (histogram 3B) is less than the amount of red blood cell bound IgG in the presence of patient serum and 1 mM Cefotetan where drug was present during the washing of the RBCs (histogram 3C).

EXAMPLE 7

Probenecid-dependent Antibodies

Figure 4A:
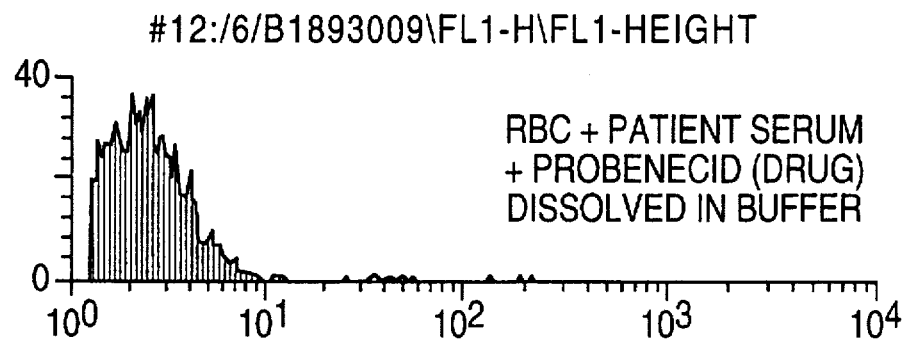
FIG. 4 shows two flow cytometry histograms demonstrating the detection of probenecid-dependent antibodies that bind red blood cells. Histogram 4A shows the amount of red blood cell bound IgG, as indicated by mean platelet immunofluorescence, in the presence of patient serum and buffer saturated with probenecid; histogram 4B represents the amount of red blood cell bound IgG in the presence of patient serum and 0.5 mM probenecid dissolved in 1.65% BSA containing buffer. The use of albumin is essential for detection of probenecid-dependent antibody.
Figure 4B:
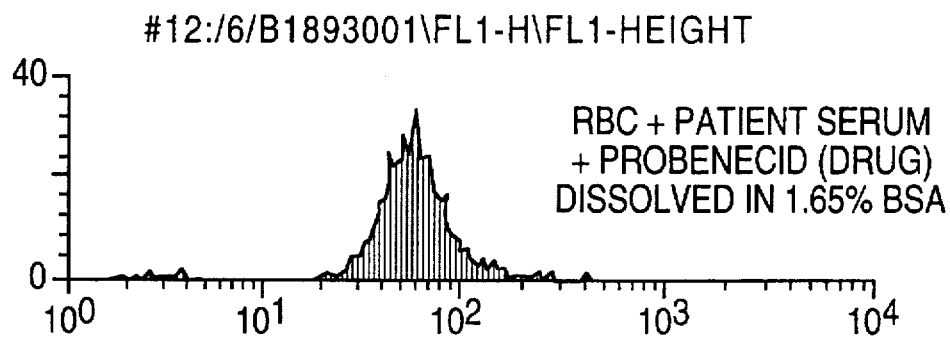

The detection of probenecid-dependent antibodies that bind red blood cells is shown in FIG. 4. The prior art had not been able to detect probenecid-dependent antibody binding to RBCs. Histogram 4A shows the amount of red blood cell bound IgG, as indicated by mean erythrocyte immunofluorescence, in the presence of patient serum and buffer saturated with probenecid; histogram 4B represents the amount of red blood cell bound IgG in the presence of patient serum and 0.5 mM probenecid dissolved in 1.65% BSA containing buffer. The use of albumin is essential for detection of probenecid-dependent antibody binding to erythrocytes.

EXAMPLE 8

Kit

The method of the present invention is suitable for use in a kit. Such a kit may comprise a receptacle being compartmentalized to receive one or more containers such as vials, tubes and the like, such containers holding samples of either granulocyte membrane proteins, erythrocytes or platelets of the invention. For example, one container may contain a blood cell or platelet preparation. A second container may contain soluble, detectably-labeled second antibody, in lyophilized form or in solution. A third container may contain a cytopenic implicated drug dissolved in a buffer.

EXAMPLE 9

Method for Detecting Drug Dependent Antibodies Capable of Reacting with Platelets, Granulocytes or Erythrocytes The reaction mixture (0.1 ml) consists of between $1\times10^6$ and $1\times10^8$, preferably $2.5\times10^7$ platelets, or between $1\times10^5$ and $1\times10^7$ granulocytes, preferably $1\times10^6$ granulocytes or between $1\times10^5$ and $1\times10^7$ RBCs, preferably $2.5\times10^6$ RBCs; 30 μl of drug at the desired concentration in 5% bovine serum albumin or 5% DMSO and 60 ul of patient serum. After incubation at room temperature for 40 minutes, the platelets are washed three times in phosphate-buffered NaCl, pH 7.4, containing 1% bovine serum and drug at the same concentration as in the primary incubation.

Washed cells or platelets are resuspended in 200 ul of a 1:150 dilution of FITC-labeled anti-human IgG F(ab')$_2$ before incubating them in the dark at room temperature for about 20 minutes. The cells or platelets are then washed once and resuspended in PBS-albumin or PBS-DMSO.

After incubating the cells or platelets with patient serum, the cells or platelets are washed and resuspended in labeled anti-human Ig F(ab')$_2$. If fluorescent label is used, the incubation takes place in the dark at room temperature for about 20–30 minutes. Labeled anti-IgG can be used at typically at a dilution of 1:10. Examples of labeled anti-human Ig F(ab')$_2$ useful for flow cytometry in the present invention are fluorescein [FITC]-labeled anti-human IgG [Fc] F(ab')$_2$ and phycoerythrin-conjugated anti-human IgM (Fc] F(ab')$_2$. After three additional washes in buffer without drug, the cells or platelets are either resuspended in PBS-albumin or PBS-DMSO and analyzed the same day or fixed in 1 percent paraformaldehyde and stored at 4° C. for up to 7 days. Sensitized, fixed platelets or fixed red blood cells may be stored, preferably for up to 7 days; granulocytes membrane proteins may be stored indefinitely. Stored cell preparations gave results comparable to those obtained with fresh cells or platelets or membrane proteins from GEP studied immediately before or after fixation.

What is claimed is:

1. A method of detecting drug-dependent antibodies in a patient, wherein a drug or a metabolite of said drug is suspected of inducing thrombocytopenia, said method comprising:

(i) separately incubating human platelets or platelet membrane protein derived from said human platelets with a serum or plasma sample from said patient, and a reagent drug or drug metabolite solution or a buffer solution, said drug or said metabolite of said drug being solubilized in said buffer solution to form said reagent drug or drug metabolite solution, said incubation being affected at a temperature and for a time sufficient to form complexes of (1) said drug or said metabolite, (2) said platelets or said platelet membrane protein, and (3) any of said drug-dependent antibodies in said serum or plasma, to form respective test and control reaction solutions; and, (ii) immunologically determining the amount of antibody bound to said platelets or said platelet membrane protein in said test and control reaction solutions;

wherein said drug-dependent antibodies are present when the amount of bound antibody is greater in the test reaction solution than in the control reaction solution; and wherein said drug or said metabolite is selected from the group consisting of acetazolamide, actinomycin, allopurinol, allylisopropylacetylurea, allylisopropylbarbiturate, alpha methyldopa, amiodarone, amphotericin B, ampicillin, amrinon, antazoline, antipyrine, apalcillin, benoxaprofen, bleomycin, butabarbitone, butoconazole, captopril, carbamazepine, carbenicillin, ceftazidine, ceftriazone, centalum, cephalexin, cephalothin, cephamandole, chenodeoxycholic acid, chlordiazepoxide, chloroquine, chlorothiazide, chlorpheniramine, chlorpropamide, chlorthalidone, cimetidine, clarithromycin, clometacine, clonazepam, clopamide, cloxacillin, cocaine, cyclophosphamide, cyclosporine A, danazol, desferrioxamine, diatrizoate, diazepam, diazoxide, diclofenac, didanosine, difluoromethylornithine, digitalis, digitoxin, digoxin, diltiazem, disulfiram, doxepin, ethambutol, etretinate, famotidine, fenoprofen, flavone-8-acetic acid, fluconazole, fluphenazine, furosemide, fusidic acid, gentamicin, glibenclamide, glymidine, haloperidol, heroin, hydrochlorothiazide, hydroxychloroquine, hydroxyquinoline, ibuprofen, imipramine, indomethacin, interferon, iocetamic acid, iopanoic acid, isoniazid, isotretinoin (vitamin A), L-dopa aminoglutethimide, levamisole, levodopa, lidocaine, lincomycin, lithium salts, meclofenamate, meprobamate, methazolamide, methicillin, methotrimeprazine, methylchlorothiazide, methylphenidate, mexiletine, mezlocillin, mianserin, minoxidil, morphine, moxalactam, N-acetylsulfanilamide sodium, nalidizic acid, naproxen, nifedipine, nimesulfide, nitrofurantoin, nitroglycerin, nomifensine, noramiopyrine, norfloxacin, novobiocin, octreotide acetate, odansetron, oxprenolol, oxyphenbutazone, oxytetracycline, p-aminosalicylate, paramethadione, penicillamine, pentagastrin, pentamidine, pentosan polysulfate, a phenothiazine, phenylbutazone, phenytoin, phthalazinol, phthalysulfathiazole, piperacillin, piperazine, piroxicam, plicamycin, polyurethane, primidone, procainamide, prochlorperazine, propranolol, propylthiouracil, ranitidine, simvastatin, sodium salicylate, spiramycin, spironolactone, stibogluconate, streptomycin, succinylsufathiazole, sulfadimethoxine, sulfaguanidine, sulfamerazine, sulfamethizole, sulfamethoxypyridazine, sulfanilamide, sulfasalazine, sulfathiazole, sulindac, suramin, thioguanin, thiomerazol, thiouracil, ticlopidine, tienilic acid, tobramycin, tolbutamide, tolmetin, trimethoprim, valproic acid and metabolites thereof.

2. A method of detecting drug-dependent antibodies in a patient, wherein a drug or a metabolite of said drug is suspected of inducing hemolytic anemia, said method comprising:

(i) separately incubating human erythrocytes or erythrocyte membrane protein derived from said human erythrocytes with a serum or plasma sample from said patient, and a reagent drug or drug metabolite solution or a buffer solution, said drug or said metabolite of said drug being solubilized in said buffer solution to form said reagent drug or drug metabolite solution, said incubation being affected at a temperature and for a time sufficient to form complexes of (1) said drug or said metabolite, (2) said erythrocytes or said erythrocyte membrane protein, and (3) any of said drug-dependent antibodies in said serum or plasma, to form respective test and control reaction solutions; and, (ii) immunologically determining the amount of antibody bound to said erythrocytes or erythrocyte membrane protein in said test and control reaction solutions;

wherein said drug-dependent antibodies are present when the amount of bound antibody is greater in the test reaction solution than in the control reaction solution; and wherein said drug or said metabolite is selected from the group consisting of acetaminophen, antazoline, carbromal, chlorpropamide, diethylstilbestrol, erythromycin, 5-fluorouracil, ibuprofen, insulin, isoniazid, melphalan, mesantoin, nalidixic acid, p-aminosalicylic acid, phenacetin, a phenothiazine, probenecid, propanil, rifampicin, streptomycin, sulfonylurea, sulindac, tetracycline, thiazides, thiopental, tolbutamide, tolmetin, triamterene, warfarin and metabolites thereof.

3. A method of detecting drug-dependent antibodies in a patient, wherein a drug or a metabolite of said drug is suspected of inducing granulocytopenia, said method comprising:

(i) separately incubating human granulocytes or granulocyte membrane protein derived from said human granulocytes with a serum or plasma sample from said patient, and a reagent drug or drug metabolite solution or a buffer solution, said drug or said metabolite of said drug being solubilized in said buffer solution to form said reagent drug or drug metabolite solution, said incubation being affected at a temperature and for a time sufficient to form complexes of (1) said drug or said metabolite, (2) said granulocytes or said granulocyte membrane protein, and (3) any of said drug-dependent antibodies in said serum or plasma, to form respective test and control reaction solutions; and, (ii) immunologically determining the amount of antibody bound to said granulocytes or granulocyte membrane protein in said test and control reaction solutions;

wherein said drug-dependent antibodies are present when the amount of bound antibody is greater in the test reaction solution than in the control reaction solution; and wherein said drug or said metabolite is selected from the group consisting of acetaminophen, acetazolamide, allopurinol, aminopyrine, amitriptyline, amoxapine, captopril, carbamazepine, carbimazole, cephalosporin, chloramphenicol, chlordiazepoxide, tolbutamide, chloroquine, chlorothiazide, chlorthalidone, cimetidine, clindamycin, clozapine, dapsone, desipramine, dipyrone, disopyramide, doxepin, ethacrynic acid, gentamicin, hydralazine, hydrochlorothiazide, imipramine, indomethacin, isoniazid, levamisole, mephenytoin, meprobamate, metamizole, methimazole, methyldopa, noramidopyrine, oxyphenbutazone, para-aminosalicylic acid, penicillamine, pentazocine, phenacetin, a phenothiazine, phenylbutazone, phenytoin, procainamide, propranolol, propylthiouracil, pyrimethamine, quinidine, ranitidine, rifampin, streptomycin, sulfonamides, tetracycline, ticlopidine, tocainide, trimethoprin-sulfamethooxazole, vancomycin and metabolites thereof.

4. The method of any one of claims 1–3, wherein said determining comprises binding a fluorescently labelled-anti-immunoglobulin specific binding partner to said bound antibodies and measuring bound fluorescence intensity by flow cytometry.

5. The method of claim 4, wherein said flow cytometry comprises measuring a ratio of the mean fluorescence intensity of said test reaction solution to the mean fluorescence intensity of said control reaction solution, and wherein a ratio of 1.5 or greater indicates the presence of said drug-dependent antibodies.

6. The method of any one of claims 1–3, wherein the concentration of said drug or said metabolite in said reagent drug or said metabolite solution is about 0.1 mM to about 1 mM.

7. The method of claim 6, wherein said drug or said metabolite is sparingly soluble in water and wherein said solution further comprises a solubilizing agent in an amount effective to solubilize said drug or said metabolite.

8. The method of claim 7, wherein said solubilizing agent is albumin or dimethyl sulfoxide.

9. The method of claim 8, wherein the effective amount of solubilizing agent is about 0.1 to 5% by weight of said reagent drug solution.

10. The method of claim 8, wherein said albumin is selected from the group consisting of ovalbumin, bovine serum albumin, equine serum albumin, ovine serum albumin, porcine serum albumin, subhuman primate serum albumin and human serum albumin.

11. The method of any one of claims 1–3, wherein said reagent drug solution containing said drug is used.

12. The method of any one of claims 1–3, wherein said drug metabolite solution containing said metabolite is used.

13. The method of claim 12, wherein said metabolite is provided as a urine sample, urine extract or serum sample from a normal person who has ingested said drug.

14. The method of any one of claims 1-3, wherein said determining is carried out in the presence of said drug or said drug metabolite.

15. The method of any one of claims 1-3, wherein said determining comprises, reacting said bound antibody with a labeled anti-immunoglobulin antibody or complement component.

16. The method of claim 15, wherein said determining is carried out in the presence of said drug or said metabolite.

17. The method of claim 1, wherein
   (a) said drug is sparingly soluble in water;
   (b) the concentration of said drug in said reagent drug solution is about 0.1 mM to about 1.0 mM;
   (c) said solution further comprises a solubilizing agent in an amount effective to solubilize said drug at said concentration; and,
   (d) said drug is selected from the group consisting of acetazolamide, carbamazepine, chlorothiazide, chlorpropamide, chlorthalidone, danazol, diazepam, diazoxide, diclofenac, digitalis, digitoxin, digoxin, diltiazem, etretinate, fenoprofen, fluconazole, furosemide, hydrochlorothiazide, ibuprofen, indomethacin, isotretinoin, levodopa, methylchlorothiazide, nalidixic acid, naproxen, nifedipine, norfloxacin, phenylbutazone, phenytoin, piroxicam, spiramycin, spironolactone, sulfadimethoxine, sulfamerazine, sulfamethizole, sulfanilamide, sulfasalazine, sulindac, thiazide, tolbutamide, tolmetin and trimethoprim.

18. The method of claim 2 wherein
   (a) said drug is sparingly soluble in water;
   (b) the concentration of said drug in said reagent drug solution is about 0.1 mM to about 1 mM;
   (c) said solution further comprises a solubilizing agent in an amount effective to solubilize said drug at said concentration; and,
   (d) said drug is selected from the group consisting of chlorothiazide, chlorpropamide, 5-fluorouracil, ibuprofen, probenecid, sulindac, tolbutamide, tolmetin and triamterene.

19. The method of claim 3, wherein
   (a) said drug is sparingly soluble in water;
   (b) the concentration of said drug in said reagent drug solution is about 0.1 mM to about 1 mM;
   (c) said solution further comprises a solubilizing agent in an amount effective to solubilize said drug at said concentration; and,
   (d) said drug is selected from the group consisting of acetazolamide, carbamazepine, chlorothiazide, chlorthalidone, clozapine, dapsone, hydrochlorothiazide, indomethacin, pentazocine, phenylbutazone, sulfamethooxazole and tolbutamide.

* * * * *